United States Patent
Hirota et al.

(10) Patent No.: US 11,061,001 B2
(45) Date of Patent: Jul. 13, 2021

(54) PHOTOACOUSTIC MEASUREMENT APPARATUS

(71) Applicant: FUJIFILM Corporation, Tokyo (JP)

(72) Inventors: Kazuhiro Hirota, Ashigarakami-gun (JP); Keiji Tsubota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 212 days.

(21) Appl. No.: 16/400,848

(22) Filed: May 1, 2019

(65) Prior Publication Data

US 2019/0257795 A1 Aug. 22, 2019

Related U.S. Application Data

(63) Continuation of application No. PCT/JP2017/033176, filed on Sep. 14, 2017.

(30) Foreign Application Priority Data

Nov. 25, 2016 (JP) .............................. JP2016-228666

(51) Int. Cl.
*G01N 29/14* (2006.01)
*G01N 29/34* (2006.01)
(Continued)

(52) U.S. Cl.
CPC ........... *G01N 29/2418* (2013.01); *A61B 8/00* (2013.01); *A61B 8/13* (2013.01); *G01N 29/00* (2013.01);
(Continued)

(58) Field of Classification Search
CPC .............. G01N 29/2431; G01N 29/24; G01N 29/2418; G01N 29/14; G01N 29/00;
(Continued)

(56) References Cited

U.S. PATENT DOCUMENTS 3,125,720 A * 3/1964 Swift ..................... G01R 31/64
324/548
4,829,530 A * 5/1989 Sato ........................ H01S 3/092
372/33
(Continued)

FOREIGN PATENT DOCUMENTS

JP 11-26860 A 1/1999
JP 11-214775 A 8/1999
(Continued)

OTHER PUBLICATIONS

International Preliminary Report on Patentability and Written Opinion of the International Searching Authority for International Application No. PCT/JP2017/033176, dated Jun. 6, 2019, with an English translation.

(Continued)

*Primary Examiner* — Jacques M Saint Surin
(74) *Attorney, Agent, or Firm* — Birch, Stewart, Kolasch & Birch, LLP

(57) ABSTRACT

There is provided a photoacoustic measurement apparatus capable of appropriately detecting a single failure state even in the single failure state so that it is possible to prevent an operation in the single failure state from continuing. There are included: a laser light source having a flash lamp and a laser medium; an excitation light source power supply having a capacitor for supplying a charge voltage to the flash lamp, a charging circuit for charging the capacitor, a first voltage dividing circuit and a second voltage dividing circuit for dividing a voltage charged in the capacitor, and a failure detection circuit that detects a failure by comparing voltages obtained by voltage division of the first voltage dividing circuit and the second voltage dividing circuit; and an ultrasound probe that detects photoacoustic waves generated (Continued)

inside a subject by emission of light emitted from the laser light source to the subject.

14 Claims, 8 Drawing Sheets

(51) Int. Cl.
    *H01S 3/092*     (2006.01)
    *G01N 29/00*     (2006.01)
    *A61B 8/00*     (2006.01)
    *H01S 3/00*     (2006.01)
    *A61B 8/13*     (2006.01)
    *G01N 29/24*     (2006.01)

(52) U.S. Cl.
    CPC .............. *G01N 29/14* (2013.01); *G01N 29/24* (2013.01); *G01N 29/2431* (2013.01); *G01N 29/34* (2013.01); *H01S 3/00* (2013.01); *H01S 3/092* (2013.01)

(58) Field of Classification Search
    CPC ........ G01N 29/343; G01N 29/34; A61B 8/00; A61B 8/13; A61B 8/5238; H01S 3/092; H01S 3/00
    USPC .......................................................... 73/632
    See application file for complete search history.

(56) References Cited

U.S. PATENT DOCUMENTS

| | | | |
|---|---|---|---|
| 5,191,261 A * | 3/1993 | Mass ...................... | H05B 41/34 315/171 |
| 2014/0316239 A1* | 10/2014 | Kasamatsu ............. | H01S 3/121 600/407 |
| 2015/0005612 A1 | 1/2015 | Suzuki | |
| 2016/0226214 A1* | 8/2016 | Ishii ....................... | H01S 3/092 |
| 2017/0012403 A1* | 1/2017 | Murakoshi ............ | H01S 3/0809 |
| 2019/0021604 A1* | 1/2019 | Ishii .................... | H01S 3/08059 |

FOREIGN PATENT DOCUMENTS

| | | | | |
|---|---|---|---|---|
| JP | 2013198368 A | * | 9/2013 | ............ Y02E 60/10 |
| JP | 2014-68493 A | | 4/2014 | |
| JP | 2015-29086 A | | 2/2015 | |

OTHER PUBLICATIONS

International Search Report for International Application No. PCT/JP2017/033176, dated Dec. 19, 2017, with an English translation.

\* cited by examiner

PHOTOACOUSTIC MEASUREMENT APPARATUS

CROSS-REFERENCE TO RELATED APPLICATIONS

This application is a Continuation of PCT International Application No. PCT/JP2017/033176 filed on Sep. 14, 2017, which claims priority under 35 U.S.C § 119(a) to Japanese Patent Application No. 2016-228666 filed on Nov. 25, 2016. Each of the above application(s) is hereby expressly incorporated by reference, in its entirety, into the present application.

BACKGROUND OF THE INVENTION

1. Field of the Invention

The present invention relates to a photoacoustic measurement apparatus comprising a laser light source that emits laser light in response to incidence of excitation light emitted from an excitation light source and in particular, relates to an excitation light source power supply that supplies a voltage to an excitation light source.

2. Description of the Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in the photoacoustic imaging, pulsed laser light, such as a laser pulse, is emitted into the living body. In the living body, the living tissue absorbs the energy of the pulsed laser light, and ultrasound waves (photoacoustic signal) are generated by adiabatic expansion due to the energy. By detecting the photoacoustic signal using an ultrasound probe or the like and forming a photoacoustic image based on the detected signal, it is possible to visualize the inside of the living body based on the photoacoustic signal.

For measurement of photoacoustic waves, it is necessary to emit pulsed laser light with high intensity in many cases. As a light source, a solid state laser device that emits pulsed laser light as a giant pulse by performing Q switch pulse oscillation is used in many cases. The laser light source has a laser rod and a flash lamp for exciting the laser rod.

The flash lamp of the laser light source is driven by a high voltage. However, as a power supply unit for supplying such a high voltage to the flash lamp, for example, JP2015-029086A has proposed a power supply unit that supplies a charge voltage charged in a capacitor to a flash lamp. In addition, JP2015-029086A has proposed a method of preventing a voltage from being unnecessarily supplied from the capacitor to the flash lamp by monitoring the terminal voltage of the capacitor.

SUMMARY OF THE INVENTION

Here, FIG. 8 is a diagram showing an example of a power supply unit that supplies a charge voltage of a capacitor to a flash lamp. In the power supply unit shown in FIG. 8, a voltage supplied from the commercial power supply is supplied to a power factor improvement circuit 106, and a charging circuit 105 charges a capacitor 101 based on the voltage output from the power factor improvement circuit 106. Then, a discharge control circuit 110 applies a gate current to a thyristor 107 according to a laser trigger signal, so that the voltage charged in the capacitor 101 is supplied to a flash lamp 111.

Then, a voltage dividing circuit 102 for monitoring the charge voltage of the capacitor 101 is connected in parallel to the capacitor 101, and a divided voltage Vmon due to the voltage dividing circuit 102 is input to a charge control unit 103 and an overcharge detection unit 104. The charge control unit 103 controls the charge voltage of the capacitor 101 by controlling the charging circuit 105 based on the difference between the input divided voltage Vmon and a reference voltage Vref set in advance. The overcharge detection unit 104 compares the input divided voltage Vmon with a maximum voltage Vmax set in advance, and outputs a control signal to the discharge control circuit 110 to stop the discharge from the capacitor 101 to the flash lamp 111 in a case where the charge voltage of the capacitor 101 exceeds the maximum voltage Vmax. In this manner, in a case where the charge voltage of the capacitor 101 exceeds the maximum voltage, safety can be secured by stopping the discharge.

However, in the case of medical equipment, it is important that, even in a single failure state, the single failure state can be recognized so as not to continue the operation in the single failure state.

In contrast, in the case of the power supply unit shown in FIG. 8, for example, in a case where a voltage dividing resistor R01 fails in the open mode, the divided voltage Vmon shows 0 V. Therefore, the charge control unit 103 recognizes that charging is not sufficient, and continues charging the capacitor 101. As a result, the capacitor 101 is overcharged, but the overcharge detection unit 104 that detects overcharge based on the same divided voltage Vmon cannot recognize the overcharge and stop discharging. Also in a case where a charge and discharge control circuit shown in FIG. 8 runs out of control due to a failure, both the charge control unit 103 and the overcharge detection unit 104 do not operate normally. Accordingly, there is a possibility that the capacitor 101 will be overcharged, and there is a possibility that the discharge control unit cannot stop the discharge.

It is an object of the present invention to provide a photoacoustic measurement apparatus capable of appropriately detecting a single failure state even in the single failure state so that it is possible to prevent an operation in the single failure state from continuing.

A photoacoustic measurement apparatus of the present invention comprises: a laser light source including an excitation light source and a laser medium, the laser light source emitting laser light from the laser medium in response to incidence of excitation light emitted from the excitation light source; an excitation light source power supply that has a capacitor for supplying a charge voltage to the excitation light source, a charging circuit for charging the capacitor, a plurality of voltage dividing circuits connected to the capacitor in parallel, wherein each of the plurality of voltage dividing circuits divides the charge voltage, and a failure detection circuit that detects a failure by comparing the divided voltages; and an ultrasound probe that detects photoacoustic waves generated inside a subject by emission of the laser light emitted from the laser light source to the subject.

In the photoacoustic measurement apparatus of the present invention described above, the excitation light source power supply may comprise a charge control circuit that controls the charge voltage of the capacitor by controlling the charging circuit and an overcharge detection circuit that detects overcharge of the capacitor. In the photoacoustic measurement apparatus of the present invention described above, the plurality of voltage dividing circuits may comprise a first voltage dividing circuit and a second voltage dividing circuit. In the photoacoustic measurement apparatus of the present invention described above, the charge control circuit may control the charge voltage of the capacitor based on a first divided voltage by the first voltage dividing circuit, and the overcharge detection circuit may detect overcharge of the capacitor based on a second divided voltage by the second voltage dividing circuit.

In the photoacoustic measurement apparatus of the present invention described above, the failure detection circuit may compare the first divided voltage output from the charge control circuit with the second divided voltage output from the overcharge detection circuit.

In the photoacoustic measurement apparatus of the present invention described above, in a case where overcharge of the capacitor is detected, the overcharge detection circuit may output a control signal for stopping voltage supply from the capacitor to the excitation light source.

In the photoacoustic measurement apparatus of the present invention described above, in a case where a failure is detected, the failure detection circuit may output a control signal for stopping the charge voltage from the capacitor to the excitation light source.

In the photoacoustic measurement apparatus of the present invention described above, it is preferable that each of the voltage dividing circuits is obtained by connecting two resistance elements in series to each other, and it is preferable that a resistance value of a resistance element on a high potential side is larger than a resistance value of a resistance element on a low potential side.

In the photoacoustic measurement apparatus of the present invention described above, the plurality of voltage dividing circuits may comprise at least three voltage dividing circuits. The failure detection circuit may detect a failure by comparing voltages obtained by the at least three voltage dividing circuits and specify a voltage dividing circuit in which a failure has occurred.

In the photoacoustic measurement apparatus of the present invention described above, it is preferable that the excitation light source power supply is a pulse forming network type flash lamp power supply.

In the photoacoustic measurement apparatus of the present invention described above, a thyristor is connected to the capacitor, and a voltage charged in the capacitor can be supplied to the excitation light source by applying a gate current to the thyristor.

In the photoacoustic measurement apparatus of the present invention described above, it is preferable that the capacitor is a capacitor bank, and it is possible to comprise a semiconductor switching element that supplies charges accumulated in the capacitor bank to the excitation light source.

According to the photoacoustic measurement apparatus of the present invention, the excitation light source power supply comprises the plurality of the voltage dividing circuits connected to the capacitor in parallel for dividing the charge voltage, and the failure detection circuit that detects a failure by comparing the divided voltages is provided. Therefore, for example, even in a single failure state such as a state in which one voltage dividing circuit fails, it is possible to appropriately detect the single failure state. As a result, it is possible to prevent the operation in the single failure state from continuing.

DESCRIPTION OF THE PREFERRED EMBODIMENTS

Figure 1:
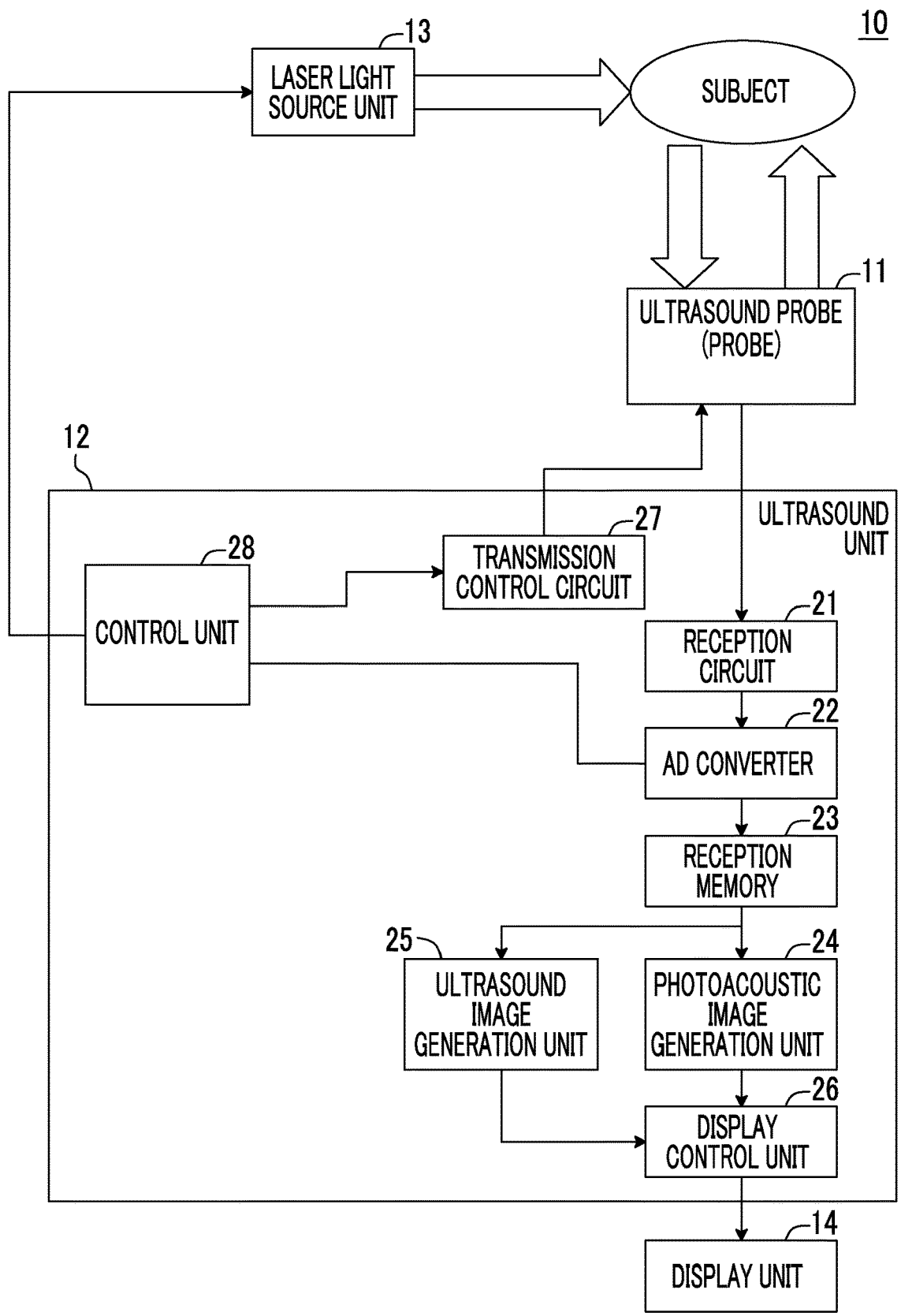
FIG. 1 is a diagram showing the schematic configuration of a photoacoustic image generation apparatus using a first embodiment of a photoacoustic measurement apparatus of the present invention.

Hereinafter, a photoacoustic image generation apparatus using a first embodiment of a photoacoustic measurement apparatus of the present invention will be described in detail with reference to the diagrams. FIG. 1 is a diagram showing the schematic configuration of a photoacoustic image generation apparatus 10 of the present embodiment. First, the overall configuration of the photoacoustic image generation apparatus 10 will be described.

The photoacoustic image generation apparatus 10 comprises an ultrasound probe (probe) 11, an ultrasound unit 12, a laser light source unit 13, and a display unit 14. In the present embodiment, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser light source unit 13 has, for example, a solid state laser light source that emits laser light, and emits laser light as measurement light that is to be emitted to a subject. The laser light source unit 13 is configured to receive a trigger signal from a control unit 28 of the ultrasound unit 12 and output laser light, for example. It is preferable that the laser light source unit 13 emits pulsed light having a pulse width of 1 ns to 100 ns as the laser light. In the present embodiment, an alexandrite laser light source using a Q switch is used as the laser light source unit 13.

The pulsed laser light emitted from the laser light source unit 13 is guided to the ultrasound probe 11 by using, for example, light guiding means such as an optical fiber, and is emitted from the ultrasound probe 11 to the subject. The emission position of the pulsed laser light is not particularly limited, and the pulsed laser light may be emitted from a place other than the ultrasound probe 11.

Within the subject, photoacoustic waves are generated due to a light absorber absorbing the energy of the emitted pulsed laser light. The ultrasound probe 11 has a plurality of ultrasound transducers arranged in a one-dimensional manner or in a two-dimensional manner, for example. The ultrasound probe 11 detects photoacoustic waves from the inside of the subject with the plurality of ultrasound transducers and outputs a photoacoustic wave signal. The ultrasound probe 11 transmits ultrasound waves to the subject, detects reflected ultrasound waves from the subject with respect to the transmitted ultrasound waves, and outputs a reflected wave signal. The ultrasound probe 11 is not limited to the linear ultrasound probe, and may be a convex ultrasound probe or a sector ultrasound probe. In the present embodiment, the ultrasound probe 11 corresponds to the ultrasound probe (a photoacoustic wave detection unit) of the present invention.

The specific configuration of the laser light source unit 13 will be described in detail later.

The ultrasound unit 12 has a reception circuit 21, an analog to digital converter (AD converter) 22, a reception memory 23, a photoacoustic image generation unit 24, an ultrasound image generation unit 25, a display control unit 26, a transmission control circuit 27, and the control unit 28.

The ultrasound unit 12 is configured to include, for example, a computer, and typically has a processor, a memory, a bus, and the like. Programs relevant to photoacoustic image generation and ultrasound image generation are installed on the memory of the ultrasound unit 12. By running the programs using the control unit 28 configured by a processor, functions of the photoacoustic image generation unit 24, the ultrasound image generation unit 25, and the display control unit 26 are realized. That is, each of these units is formed by the memory on which the programs are installed and the processor.

The configuration of the hardware of the ultrasound unit 12 is not particularly limited, and can be realized by appropriately combining a plurality of integrated circuits (ICs), processors, application specific integrated circuits (ASICs), field-programmable gate arrays (FPGAs), memories, and the like.

The reception circuit 21 receives the photoacoustic wave signal and the reflected wave signal output from the ultrasound probe 11. Typically, the reception circuit 21 includes a low noise amplifier, a variable gain amplifier, and a low pass filter. The photoacoustic wave signal and the reflected wave signal output from the ultrasound probe 11 are amplified by the low noise amplifier, and then the gain is adjusted according to the depth by the variable gain amplifier and high frequency components are cut by the low pass filter.

The AD converter 22 converts the photoacoustic wave signal and the reflected wave signal received by the reception circuit 21 into digital signals. The AD converter 22 samples the photoacoustic wave signal and the reflected wave signal at predetermined sampling periods based on, for example, a sampling clock signal having a predetermined period. The AD converter 22 stores the sampled photoacoustic wave signal and reflected wave signal (sampling data) in the reception memory 23. The reception circuit 21 and the AD converter 22 may be formed as, for example, one IC, or may be formed as individual ICs.

The photoacoustic image generation unit 24 generates a photoacoustic image based on the photoacoustic wave signal stored in the reception memory 23. The generation of a photoacoustic image includes, for example, image reconstruction such as a Fourier transfer algorithm (FTA) method or a delayed addition (phase matching addition) method, detection, and logarithmic conversion.

The ultrasound image generation unit 25 generates an ultrasound image based on the reflected wave signal stored in the reception memory 23. The generation of an ultrasound image also includes image reconstruction such as phase matching addition, detection, and logarithmic conversion.

The control unit 28 controls each unit of the photoacoustic image generation apparatus 10, and comprises a trigger control circuit (not shown) in the present embodiment. The trigger control circuit transmits a laser trigger signal to the laser light source unit 13, for example, at the start of the photoacoustic image generation apparatus 10. Therefore, in the laser light source unit 13, a flash lamp 52 to be described is lit to start the excitation of a laser rod 51. Then, the excitation state of the laser rod 51 is maintained, so that the laser light source unit 13 can output pulsed laser light.

Then, at the time of generating a photoacoustic image, the control unit 28 transmits a Qsw trigger signal from the trigger control circuit to the laser light source unit 13. That is, the control unit 28 controls the output timing of the pulsed laser light from the laser light source unit 13 using the Qsw trigger signal. In the present embodiment, the control unit 28 transmits a sampling trigger signal to the AD converter 22 simultaneously with the transmission of the Qsw trigger signal. The sampling trigger signal is a signal of the start timing of the sampling of the photoacoustic wave signal in the AD converter 22. Thus, it is possible to sample the photoacoustic wave signal in synchronization with the output of laser light by using the sampling trigger signal.

At the time of generating an ultrasound image, the control unit 28 transmits an ultrasound wave transmission trigger signal for instructing the transmission control circuit 27 to transmit ultrasound waves. In a case where the trigger signal is received, the transmission control circuit 27 causes the ultrasound probe 11 to transmit ultrasound waves. After the transmission of ultrasound waves, the ultrasound probe 11 detects reflected ultrasound waves from the subject and outputs a reflected wave signal.

The reflected wave signal output from the ultrasound probe 11 is input to the AD converter 22 through the reception circuit 21. The control unit 28 transmits a sampling trigger signal to the AD converter 22 according to the timing of ultrasound wave transmission, thereby starting the sampling of the reflected wave signal.

The control unit 28 controls each unit so that the photoacoustic image and the ultrasound image are acquired at the same timing, for example. The same timing referred to herein does not mean completely the same timing but means that the photoacoustic image and the ultrasound image are sequentially acquired within a short time of a predetermined timing. That is, the photoacoustic image and the ultrasound image are sequentially acquired at the same frame rate.

For example, the display control unit 26 displays the photoacoustic image and the ultrasound image separately on the display unit 14, or displays a composite image of the photoacoustic image and the ultrasound image on the display unit 14. The display control unit 26 performs image combination by superimposing the photoacoustic image and the ultrasound image, for example.

Figure 2:
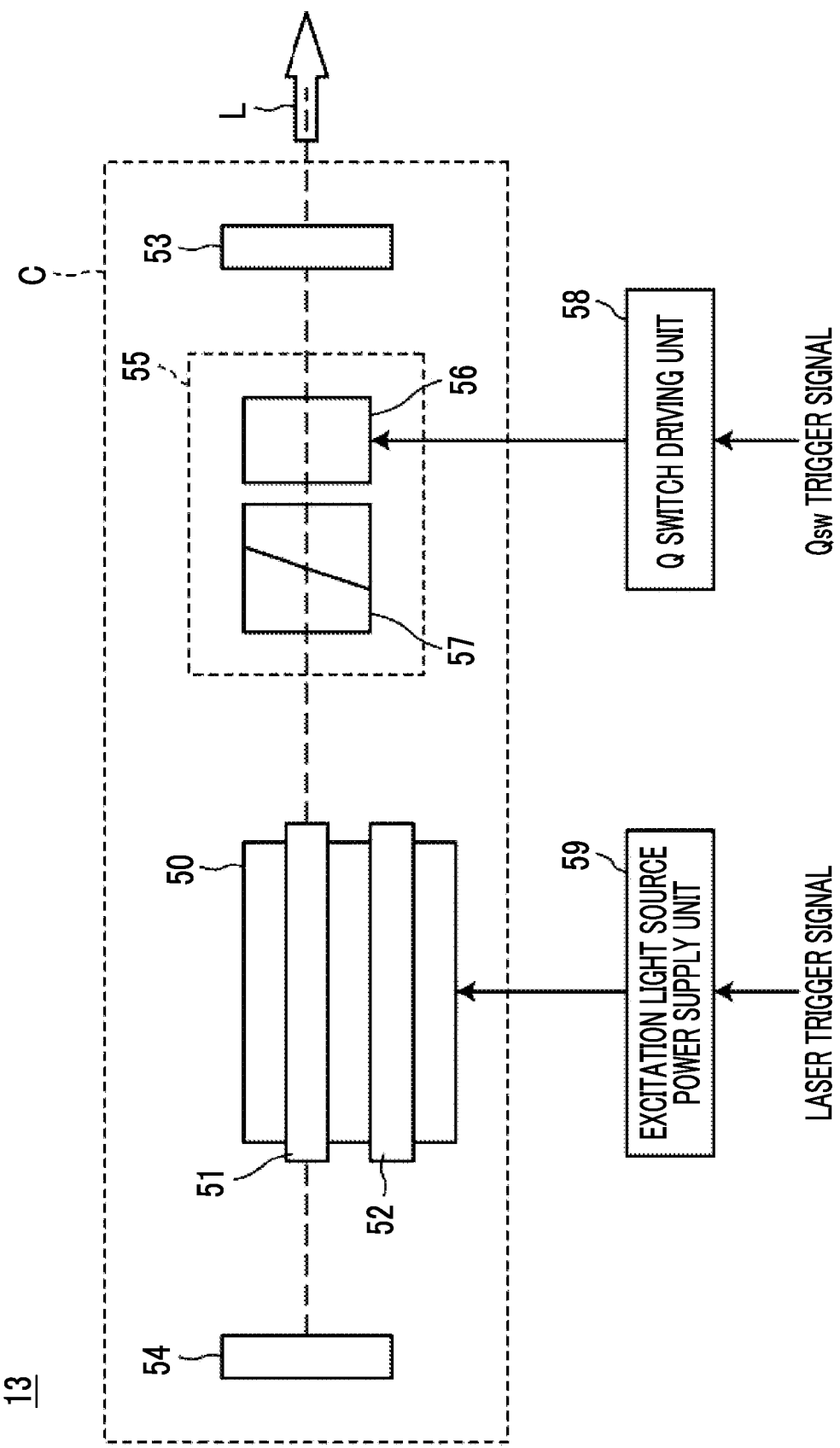
FIG. 2 is a diagram showing a specific configuration of a laser light source unit.

Next, the specific configuration of the above laser light source unit 13 will be described. FIG. 2 is a diagram showing the specific configuration of the laser light source unit 13.

As shown in FIG. 2, the laser light source unit 13 of the present embodiment comprises the laser rod 51, the flash lamp 52, a laser chamber 50, a first mirror 53, a second mirror 54, a Q value changing unit 55, a Q switch driving unit 58, and an excitation light source power supply unit 59. In the present embodiment, a laser light source of the present invention is formed by the laser rod 51, the flash lamp 52, the laser chamber 50, the first mirror 53, the second mirror 54, and the Q value changing unit 55.

The flash lamp 52 emits excitation light. The flash lamp 52 is intermittently driven by the high voltage output from the excitation light source power supply unit 59 (the excitation light source power supply), and emits pulsed excitation light. The flash lamp 52 corresponds to an excitation light source of the present invention. The excitation light source is not limited to the flash lamp 52, and other excitation light sources may be used.

The laser rod 51 is a bar-shaped laser medium, and receives the excitation light emitted from the flash lamp 52 and emits laser light. As the laser rod 51, for example, alexandrite crystal can be used, but other known laser mediums, such as Nd:YAG crystal, can be used without being limited thereto. In the present embodiment, the laser rod 51 corresponds to a laser medium of the present invention.

The laser rod 51 and the flash lamp 52 are housed in the laser chamber 50. A reflection surface is provided inside the laser chamber 50, and the light emitted from the flash lamp 52 is directly emitted to the laser rod 51 or is reflected on the reflection surface and emitted to the laser rod 51. The inside of the laser chamber 50 may be a diffuse reflection surface.

The first mirror 53 and the second mirror 54 are arranged along the optical axis of the laser rod 51. The first mirror 53 and the second mirror 54 are arranged so as to face each other with the laser rod 51 interposed therebetween. The laser light emitted from the laser rod 51 is reflected by the first mirror 53 and the second mirror 54 and reciprocates between the first mirror 53 and the second mirror 54. That is, a resonator C is formed by the first mirror 53 and the second mirror 54. The first mirror 53 is an output coupler (OC). Then, by the control of the Q value of the resonator C by the Q value changing unit 55, pulsed laser light L is emitted from the first mirror 53.

In the present embodiment, the first mirror 53 and the second mirror 54 are arranged along the optical axis of the laser rod 51 to form the optical path of the resonator C in a linear shape. However, the present invention is not limited thereto, and a prism or the like may be provided on the optical path between the first mirror 53 and the second mirror 54 to bend the optical axis.

The Q value changing unit 55 is inserted in the optical path of the resonator C to change the Q value of the resonator. In the present embodiment, the Q value changing unit 55 is disposed between the first mirror 53 and the laser rod 51. However, the Q value changing unit 55 may be disposed between the laser rod 51 and the second mirror 54 without being limited thereto. The Q value changing unit 55 comprises a Q switch 56 and a polarizer 57.

The Q switch 56 changes the Q value of the resonator C by changing the polarization state of light transmitted therethrough according to the applied voltage. As the Q switch 56, it is possible to use an electro-optical element that changes the polarization state of light transmitted therethrough according to the applied voltage. For example, a Pockels cell can be used as the Q switch 56.

The Q switch 56 changes the state of the resonator C to a low Q state in a case where a first voltage corresponding to Q switch OFF is applied. The low Q state is a state in which the Q value of the resonator C is lower than a laser oscillation threshold value. The Q switch OFF refers to the state of the Q switch 56 that changes the state of the resonator C to the low Q state as described above. The Q switch 56 of the present embodiment functions as a quarter wavelength plate in a case where the first voltage is applied.

The Q switch 56 changes the state of the resonator C to a high Q state in a case where a second voltage corresponding to Q switch ON is applied. The high Q state is a state in which the Q value of the resonator C is higher than the laser oscillation threshold value. The Q switch ON refers to the state of the Q switch 56 that changes the state of the resonator C to the high Q state as described above. The Q switch 56 of the present embodiment does not change the polarization state of light transmitted therethrough in a case where the second voltage is applied.

The relationship between the first voltage and the second voltage is that the absolute value of the first voltage is larger than the absolute value of the second voltage. The voltage may be a positive voltage or a negative voltage. The second voltage can be set to, for example, 0 V (no voltage applied).

The polarizer 57 is disposed between the laser rod 51 and the Q switch 56. The polarizer 57 allows only linearly polarized light in a predetermined direction to pass therethrough. As the polarizer 57, for example, a beam splitter that transmits linearly polarized light in a predetermined direction and reflects linearly polarized light in a direction perpendicular to the predetermined direction can be used. In the present embodiment, a beam splitter that transmits p-polarized light and reflects s-polarized light is used as the polarizer 57. The polarizer 57 may be omitted in a case where the laser rod 51 itself has polarized light selectivity, such as a case where alexandrite crystal is used as the laser rod 51.

Specifically, in a case where the first voltage is applied to the Q switch 56, the Q switch 56 functions as a quarter wavelength plate as described above. First, p-polarized light incident on the polarizer 57 from the laser rod 51 passes through the polarizer 57, and becomes circularly polarized light at the time of passing through the Q switch 56. Then, the circularly polarized light transmitted through the Q switch 56 is reflected by the first mirror 53 and is then incident on the Q switch 56 again from the opposite direction. The circularly polarized light incident on the Q switch 56 in the opposite direction becomes linearly polarized light again at the time of passing through the Q switch 56, but is incident on the polarizer 57 as s-polarized light rotated by 90° and is emitted to the outside of the optical path of the resonator C. Accordingly, laser oscillation does not occur in the laser rod 51.

On the other hand, in a case where the voltage applied to the Q switch 56 is the second voltage (0 V), the p-polarized light incident on the polarizer 57 from the laser rod 51 passes through the Q switch 56 without changing the polarization state and is reflected by the first mirror 53. The light reflected by the first mirror 53 also passes through the Q switch 56 without changing the polarization state, further passes through the polarizer 57, and returns to the laser rod 51. In this manner, laser oscillation occurs.

As described above, in a case where the first voltage is applied to the Q switch 56, the Q switch 56 is made to function as a quarter wavelength plate, so that the laser light emitted from the laser rod 51 is emitted to the outside of the optical path of the resonator C and as a result, the resonator C can be changed to the low Q state. On the other hand, in a case where the second voltage is applied to the Q switch 56, the Q switch 56 is not made to function as a quarter wavelength plate, so that the incident laser light passes through the Q switch 56 as it is and as a result, the resonator C can be changed to the high Q state.

The Q switch driving unit 58 drives the Q switch 56 by applying the first voltage and the second voltage described above to the Q switch 56. The Q switch driving unit 58 applies a voltage to the Q switch 56 based on the signal output from the control unit 28 of the ultrasound unit 12.

Figure 3:
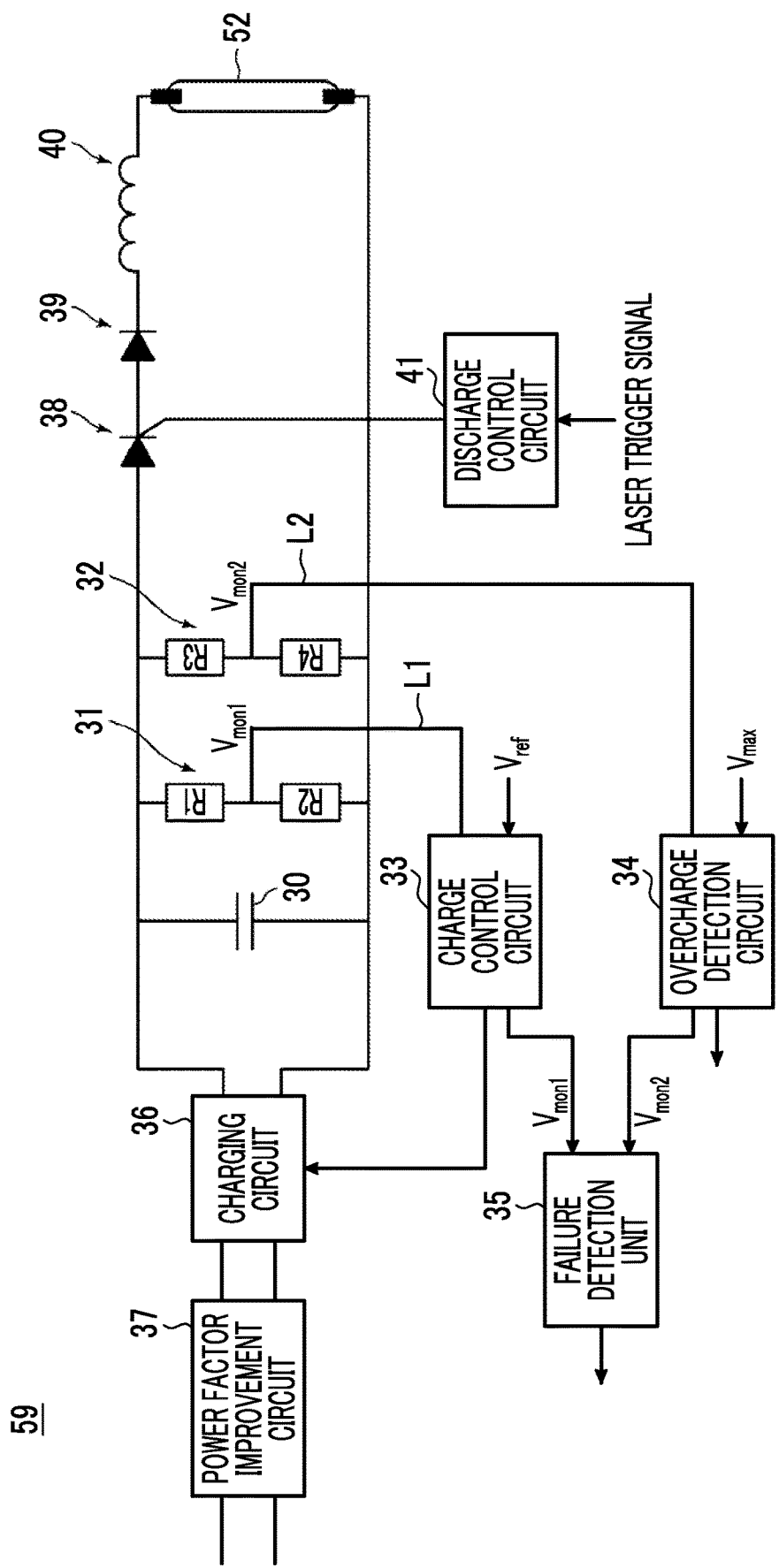
FIG. 3 is a diagram showing a specific configuration of an excitation light source power supply unit.

The excitation light source power supply unit 59 applies a high voltage to the flash lamp 52 according to the laser trigger signal output from the ultrasound unit 12. FIG. 3 is a diagram showing the specific configuration of the excitation light source power supply unit 59.

As shown in FIG. 3, the excitation light source power supply unit 59 comprises a capacitor 30, a first voltage dividing circuit 31, a second voltage dividing circuit 32, a charge control circuit 33, an overcharge detection circuit 34, a failure detection unit 35 (a failure detection circuit), a charging circuit 36, a power factor improvement circuit 37, a thyristor 38, a diode 39, an inductor 40, and a discharge control circuit 41.

The capacitor 30 supplies a voltage charged by the charging circuit 36 to the flash lamp 52. Based on the voltage supplied from the commercial power supply through the power factor improvement circuit 37, the charging circuit 36 supplies a voltage to the capacitor 30 to charge the capacitor 30. As the charging circuit 36 and the power factor improvement circuit 37, a general known circuit can be used.

The first voltage dividing circuit 31 is connected in parallel to the capacitor 30, and comprises a first resistance element R1 and a second resistance element R2. The first resistance element R1 and the second resistance element R2 are connected in series to each other. Then, a wiring L1 is connected between the first resistance element R1 and the second resistance element R2, and a first divided voltage Vmon1 determined by the resistance value of the first resistance element R1 and the resistance value of the second resistance element R2 is output to the wiring L1. The charge control circuit 33 is connected to the output destination of the wiring L1, and the first divided voltage Vmon1 is supplied to the charge control circuit 33.

The second voltage dividing circuit 32 is connected in parallel to the capacitor 30 and the first voltage dividing circuit 31, and comprises a third resistance element R3 and a fourth resistance element R4. The third resistance element R3 and the fourth resistance element R4 are connected in series to each other. Then, a wiring L2 is connected between the third resistance element R3 and the fourth resistance element R4, and a second divided voltage Vmon2 determined by the resistance value of the third resistance element R3 and the resistance value of the fourth resistance element R4 is output to the wiring L2. The overcharge detection circuit 34 is connected to the output destination of the wiring L2, and the second divided voltage Vmon2 is supplied to the overcharge detection circuit 34.

In the present embodiment, it is assumed that the relationship among the resistance value r1 of the first resistance element R1, the resistance value r2 of the second resistance element R2, the resistance value r3 of the third resistance element R3, and the resistance value r4 of the fourth resistance element R4 is r1:r2=r3:r4 and the first divided voltage Vmon1 and the second divided voltage Vmon2 have approximately the same magnitude. However, the relationship is not limited thereto, and r1:r2 and r3:r4 may be different.

In the present embodiment, r1:r2=r3:r4=99:1 is assumed. That is, the resistance value r1 of the first resistance element R1 on the high potential side is larger than the resistance value r2 of the second resistance element R2 on the low potential side, and the resistance value r3 of the third resistance element R3 on the high potential side is larger than the resistance value r4 of the fourth resistance element R4 on the low potential side.

Therefore, for example, in a case where the voltage charged in the capacitor 30 is 600 V, the first divided voltage Vmon1 and the second divided voltage Vmon2 are about 6 V. In a case where the charge control circuit 33 to which the first divided voltage Vmon1 is supplied and the overcharge detection circuit 34 to which the second divided voltage Vmon2 is supplied are formed by, for example, an integrated circuit (IC), a general-purpose IC can be used by setting the first divided voltage Vmon1 and the second divided voltage Vmon2 to about 6 V as described above. As a result, it is possible to reduce the cost. However, r1:r2 and r3:r4 are not limited to 99:1, and can be appropriately changed according to the allowable input voltages of the charge control circuit 33 and the overcharge detection circuit 34 that are supply destinations of the first divided voltage Vmon1 and the second divided voltage Vmon2. By setting the values of r1 and r3 to be smaller than 99 and providing an attenuator, an operational amplifier, and the like at a stage before the charge control circuit 33 and the overcharge detection circuit 34, voltages input to the charge control circuit 33 and the overcharge detection circuit 34 may be reduced to the allowable input voltages.

The charge control circuit 33 controls the charge voltage of the capacitor 30 by controlling the charging circuit 36. Specifically, the charge control circuit 33 of the present embodiment calculates a difference voltage between the input first divided voltage Vmon1 and the reference voltage Vref set in advance and controls the charging circuit 36 based on the difference voltage, thereby performing control so that the charge voltage of the capacitor 30 becomes a voltage value set in advance. That is, the charge control circuit 33 of the present embodiment controls the charge voltage of the capacitor 30 so as to be 600 V. The charge control circuit 33 outputs the input first divided voltage Vmon1 to the failure detection unit 35.

The overcharge detection circuit 34 detects overcharge of the capacitor 30. Specifically, based on the input second divided voltage Vmon2 and the maximum voltage Vmax set in advance, the overcharge detection circuit 34 of the present embodiment detects that the charge voltage of the capacitor 30 exceeds the maximum voltage Vmax to cause overcharge. Then, in a case where the overcharge of the capacitor 30 is detected, the overcharge detection circuit 34 outputs a control signal to the discharge control circuit 41 to stop power supply (discharge) from the capacitor 30 to the flash lamp 52. In the present embodiment, the maximum voltage Vmax is set to 600 V. In addition, the overcharge detection circuit 34 outputs the input second divided voltage Vmon2 to the failure detection unit 35.

The failure detection unit 35 detects a failure by comparing the input first divided voltage Vmon1 and the input second divided voltage Vmon2 with each other. In the present embodiment, in the case of a normal condition, the first divided voltage Vmon1 and the second divided voltage Vmon2 input to the failure detection unit 35 are the same voltage, and the difference therebetween is zero. However, for example, in a case where the first resistance element R1 fails in the open mode, the first divided voltage Vmon1 becomes zero. In contrast, since the second divided voltage Vmon2 remains 6 V as described above, a failure is detected based on the difference. Similarly, even in a case where the third resistance element R3 fails in the open mode, the failure detection unit 35 detects a failure from the difference between the first divided voltage Vmon1 and the second divided voltage Vmon2.

Then, in a case where a failure in the excitation light source power supply unit 59 is detected, the failure detection unit 35 outputs a control signal to the discharge control circuit 41 to stop power supply (discharge) from the capacitor 30 to the flash lamp 52. Alternatively, the failure detection unit 35 stops the entire photoacoustic image generation apparatus 10 by outputting a control signal to the control unit 28 of the ultrasound unit 12.

Here, a difference from a failsafe mechanism having only redundancy by simply connecting the voltage dividing circuits in parallel without providing the failure detection unit 35 that compares the first divided voltage Vmon1 with the second divided voltage Vmon2 unlike in the present embodiment is considered. For example, in a case where the third resistance element R3 fails in the open mode as described above, the overcharge detection circuit 34 does not operate normally, but the first divided voltage Vmon1 is a normal value. Therefore, the failure of the second voltage dividing circuit 32 is not recognized, and the normal operation is continued.

In such a state, for example, in a case where a semiconductor switch used in the charging circuit 36 fails in the ON state, the capacitor 30 is charged unlimitedly. At this time, the charge control circuit 33 tries to stop charging by the charging circuit 36 based on the first divided voltage Vmon1. However, since the charging circuit 36 itself has failed, the operation of the laser light source unit 13 cannot be stopped. In addition, since the overcharge detection circuit 34 does not already operate normally as described above, the operation of the laser light source unit 13 cannot be stopped. That is, it is not possible to safely stop the apparatus with the failsafe mechanism having only redundancy by simply connecting the voltage dividing circuits in parallel.

In contrast, in the present embodiment, the failure detection unit 35 compares the first divided voltage Vmon1 with the second divided voltage Vmon2 and detects a failure based on the comparison result. Therefore, even in a case where the third resistance element R3 fails in the open mode, the operation of the laser light source unit 13 can be stopped immediately.

In the above description, the case where failures of the first voltage dividing circuit 31 and the second voltage dividing circuit 32 are detected. However, the present embodiment is not limited to the failures of these voltage dividing circuits. For example, even in a case where the charge control circuit 33 fails, since the first divided voltage Vmon1 output from the charge control circuit 33 becomes an abnormal value, it is possible to immediately detect the failure. In addition, even in a case where the overcharge detection circuit 34 fails, since the second divided voltage Vmon2 output from the overcharge detection circuit 34 becomes an abnormal value, it is possible to immediately detect the failure.

The thyristor 38 is connected between the capacitor 30 and the flash lamp 52. The thyristor 38 has a property that the thyristor 38 is turned ON by applying a gate current thereto and is not turned OFF until the current from the anode terminal stops once turned ON. Therefore, in the present embodiment, by applying the gate current to the thyristor 38 by the discharge control circuit 41, all the charges stored in the capacitor 30 are supplied to the flash lamp 52. The discharge control circuit 41 causes a gate current to flow through the thyristor 38 according to the laser trigger signal output from the control unit 28 of the ultrasound unit 12.

Figure 4:
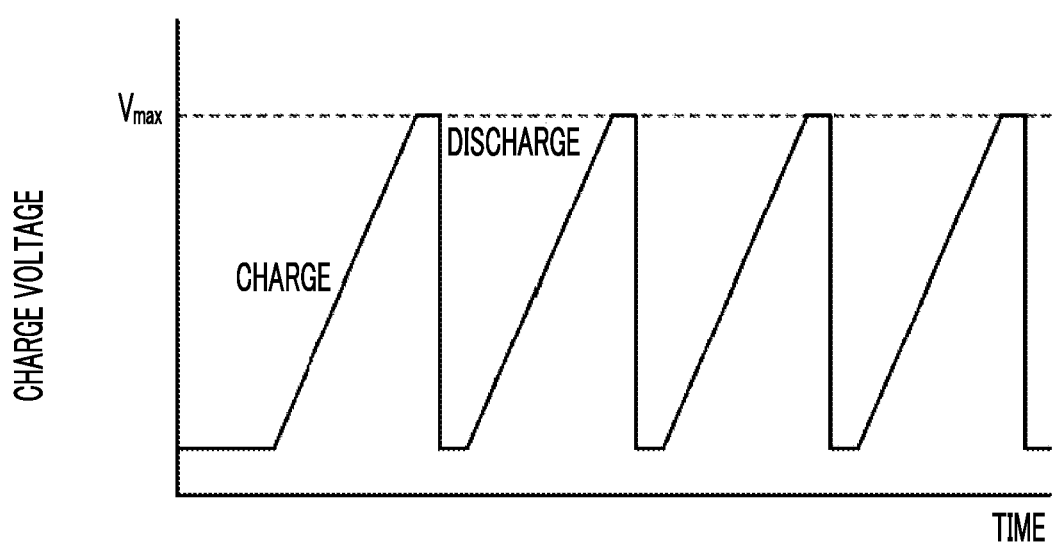
FIG. 4 is a diagram showing a voltage change of a capacitor while an excitation light source power supply unit of the first embodiment is operating normally.

FIG. 4 shows a voltage change of the capacitor 30 during a normal operation. As shown in FIG. 4, the capacitor 30 is charged by the charging circuit 36, the charge voltage of the capacitor 30 is controlled to be Vmax=600 V by the charge control circuit 33, and the capacitor 30 is discharged by the gate current flowing through the thyristor 38 by the discharge control circuit 41.

The diode 39 and the inductor 40 are connected between the thyristor 38 and the flash lamp 52. A pulse forming network is formed by the capacitor 30 and the inductor 40, a pulse current corresponding to the charge voltage of the capacitor 30 is supplied to the flash lamp 52, and pulsed excitation light is emitted from the flash lamp 52. Assuming that the capacitance of the capacitor 30 is C and the charge voltage of the capacitor 30 is Vc, excitation energy E of the flash lamp 52 is calculated by $E=(\frac{1}{2})CVc^2$. The pulse width T of the pulsed excitation light is calculated by $T=3\times LC^{1/3}$.

The charge control circuit 33, the overcharge detection circuit 34, the failure detection unit 35, and the discharge control circuit 41 may be formed as one IC, or may be formed as a plurality of ICs, or may be formed by an ASIC, an FPGA, and the like. The failure detection unit 35 compares the first divided voltage Vmon1 with the second divided voltage Vmon2. However, for the comparison circuit, an IC may be used, or a comparator may be formed using discrete components.

According to the photoacoustic image generation apparatus 10 of the embodiment described above, the excitation light source power supply unit 59 of the laser light source unit 13 comprises the first voltage dividing circuit 31 and the second voltage dividing circuit 32 that divide the voltage charged in the capacitor 30, and the failure detection unit 35 that detects a failure by comparing the voltages obtained by voltage division of the first voltage dividing circuit 31 and the second voltage dividing circuit 32 is provided. Therefore, for example, even in a single failure state such as a state in which one voltage dividing circuit fails, it is possible to appropriately detect the single failure state. As a result, it is possible to prevent the operation in the single failure state from continuing.

Figure 5:
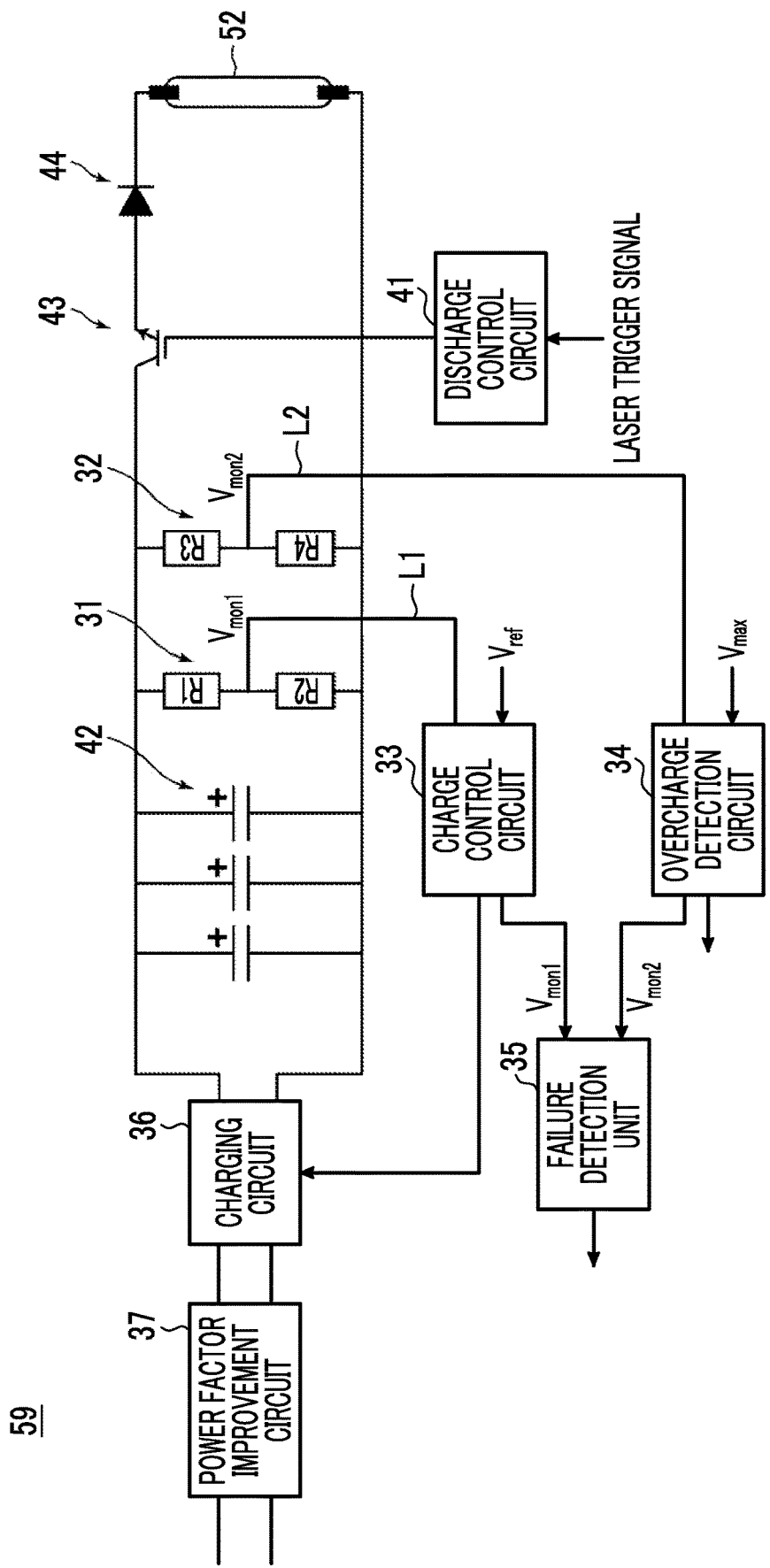
FIG. 5 is a diagram showing a specific configuration of an excitation light source power supply unit of a second embodiment.

Next, the photoacoustic image generation apparatus 10 using a second embodiment of the photoacoustic measurement apparatus of the present invention will be described. In the photoacoustic image generation apparatus 10 of the second embodiment, the configuration of the excitation light source power supply unit 59 is different from that in the photoacoustic image generation apparatus 10 of the first embodiment, and the other configurations are the same as those in the photoacoustic image generation apparatus 10 of the first embodiment. FIG. 5 is a diagram showing the specific configuration of the excitation light source power supply unit 59 of the photoacoustic image generation apparatus 10 of the second embodiment. In FIG. 5, the same components as in the excitation light source power supply unit 59 of the first embodiment are denoted by the same reference numerals.

Although the excitation light source power supply unit 59 of the first embodiment is a pulse forming network type flash lamp power supply, the excitation light source power supply unit 59 of the second embodiment is a direct drive type flash lamp power supply.

Specifically, in the excitation light source power supply unit 59 of the second embodiment, a large-capacity capacitor bank 42 is provided instead of the capacitor 30 of the excitation light source power supply unit 59 of the first embodiment. In the excitation light source power supply unit 59 of the second embodiment, an insulated gate bipolar transistor (IGBT) 43 and a diode 44 are provided between the capacitor bank 42 and the flash lamp 52. The IGBT 43 is a semiconductor switching element, and supplies charges accumulated in the capacitor bank 42 to the flash lamp 52. Only while the IGBT 43 is in the ON state, discharge from the capacitor bank 42 to the flash lamp 52 occurs. Since the discharge from the capacitor bank 42 to the flash lamp 52 is controlled by ON and OFF of the IGBT 43, the accuracy of the capacitance of the capacitor is not important compared with the pulse forming network (PFN) method of the first embodiment, and the large-capacity capacitor bank 42 formed of an electrolytic capacitor is used.

Figure 6:
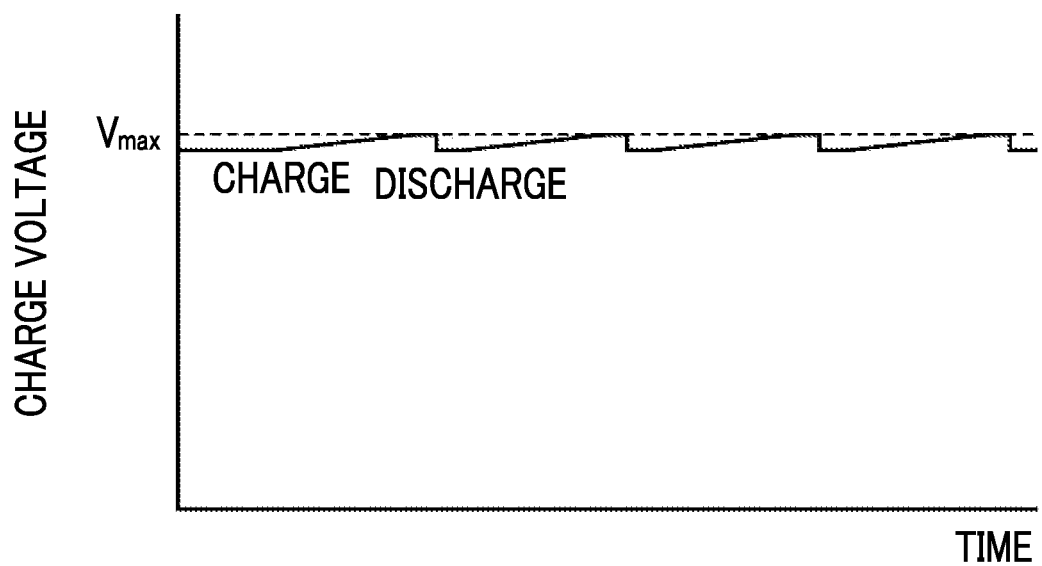
FIG. 6 is a diagram showing a voltage change of a capacitor while an excitation light source power supply unit of the second embodiment is operating normally.

FIG. 6 shows a voltage change of the capacitor bank 42 during a normal operation. As shown in FIG. 6, the capacitor bank 42 is charged by the charging circuit 36, the charge voltage of the capacitor 30 is controlled to be Vmax=600 V by the charge control circuit 33, and the capacitor bank 42 is discharged by turning on the IGBT 43 by the discharge control circuit 41.

The other configurations of the excitation light source power supply unit 59 of the second embodiment are the same as those of the excitation light source power supply unit 59 of the first embodiment.

Figure 7:
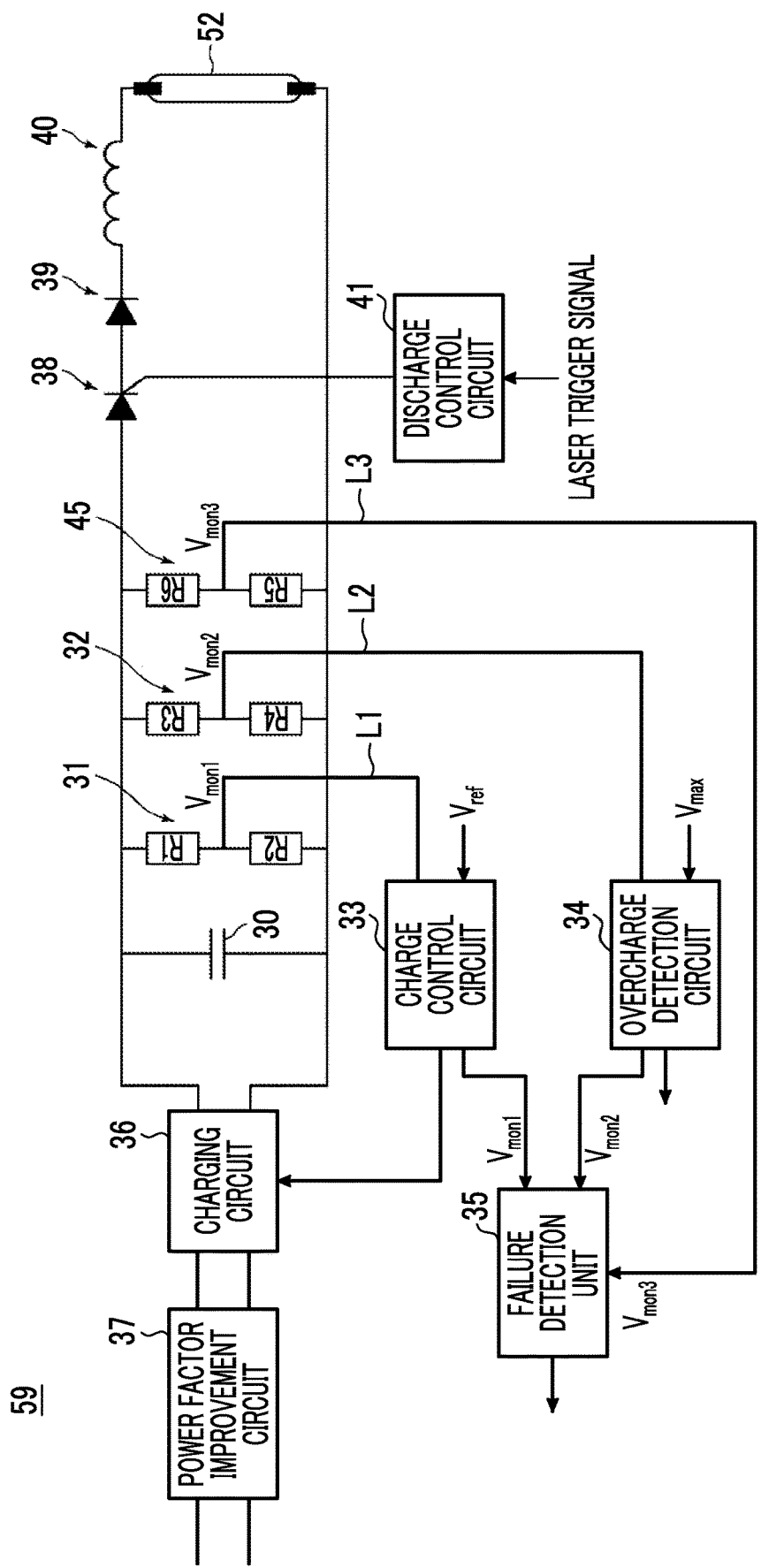
FIG. 7 is a diagram showing a specific configuration of an excitation light source power supply unit of a third embodiment.
Figure 8:
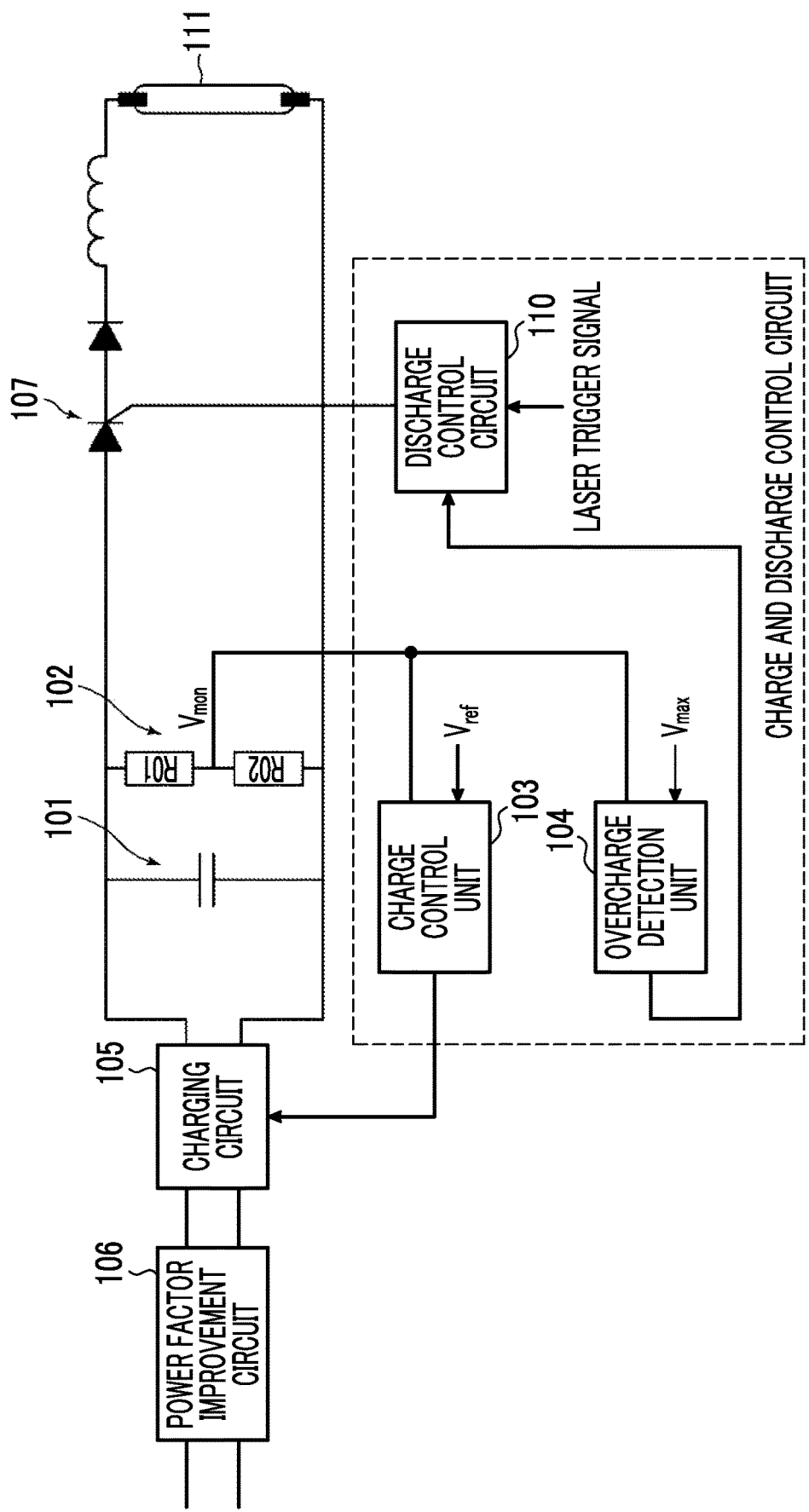
FIG. 8 is a diagram showing an example of a power supply unit that supplies a charge voltage of a capacitor to a flash lamp.

Next, the photoacoustic image generation apparatus 10 using a third embodiment of the photoacoustic measurement apparatus of the present invention will be described. In the photoacoustic image generation apparatus 10 of the third embodiment, the configuration of the excitation light source power supply unit 59 is different from that in the photoacoustic image generation apparatus 10 of the first embodiment, and the other configurations are the same as those in the photoacoustic image generation apparatus 10 of the first embodiment. FIG. 7 is a diagram showing the specific configuration of the excitation light source power supply unit 59 of the photoacoustic image generation apparatus 10 of the third embodiment. In FIG. 7, the same components as in the excitation light source power supply unit 59 of the first embodiment are denoted by the same reference numerals.

Although the parallel voltage dividing circuits are provided in the excitation light source power supply unit 59 of the first embodiment, the excitation light source power supply unit 59 of the third embodiment further comprises a third voltage dividing circuit 45.

The third voltage dividing circuit 45 is connected in parallel to the capacitor 30, the first voltage dividing circuit 31, and the second voltage dividing circuit 32, and comprises a fifth resistance element R5 and a sixth resistance element R6. The fifth resistance element R5 and the sixth resistance element R6 are connected in series to each other. Then, a wiring L3 is connected between the fifth resistance element R5 and the sixth resistance element R6, and a third divided voltage Vmon3 determined by the resistance value of the fifth resistance element R5 and the resistance value of the sixth resistance element R6 is output to the wiring L3. The failure detection unit 35 is connected to the output destination of the wiring L3, and the third divided voltage Vmon3 is supplied to the failure detection unit 35.

In the present embodiment, it is assumed that the relationship among the resistance value r1 of the first resistance element R1, the resistance value r2 of the second resistance element R2, the resistance value r3 of the third resistance element R3, the resistance value r4 of the fourth resistance element R4, the resistance value r5 of the fifth resistance element R5, and the resistance value r6 of the sixth resistance element R6 is r1:r2=r3:r4=r5:r6 and the first divided voltage Vmon1, the second divided voltage Vmon2, and the third divided voltage Vmon3 have approximately the same magnitude.

Then, although the failure detection unit 35 of the first embodiment detects a failure based on the difference between the first divided voltage Vmon1 and the second divided voltage Vmon2, the failure detection unit 35 of the third embodiment further uses the third divided voltage Vmon3 to specify a location where the failure has occurred.

Specifically, as described above, for example, in a case where the first resistance element R1 fails in the open mode, the first divided voltage Vmon1 is 0 V but the second divided voltage Vmon2 remains a normal voltage value, and accordingly, it is possible to detect that a failure has occurred. Furthermore, the third divided voltage Vmon3 is compared with the first divided voltage Vmon1, and the third divided voltage Vmon3 is compared with the second divided voltage Vmon2. Then, since the third divided voltage Vmon3 and the first divided voltage Vmon1 are different voltage values and the third divided voltage Vmon3 and the second divided voltage Vmon2 are the same voltage value, it is possible to determine that the first divided voltage Vmon1 is an abnormal value. Accordingly, it is possible to specify that the first voltage dividing circuit 31 has failed.

In a case where three or more voltage dividing circuits are provided as described above, by comparing the respective divided voltages with each other and determining an abnormal voltage value by majority vote, it is possible to specify that a failure has occurred in the voltage dividing circuit that is outputting the divided voltage of the abnormal voltage value. The information of the specified voltage dividing circuit may be displayed on the display unit 14 by the display control unit 26, for example, so that the user is notified of the information.

In the first to third embodiments described above, each of the first voltage dividing circuit 31, the second voltage dividing circuit 32, and the third voltage dividing circuit 45 is formed by two resistance elements. However, the configuration of each voltage dividing circuit is not limited thereto, and other circuit configurations may be adopted. For example, three or more resistance elements may be connected in series to form a voltage dividing circuit. Specifically, in a case where the first resistance element R1 and the second resistance element R2 of the first voltage dividing circuit 31 are 990 kΩ and 1 kΩ, respectively, the first resistance element R1 may be replaced with a circuit in which three resistance elements of 330 kΩ are connected in series to each other.

Alternatively, one of the two resistance elements in the first voltage dividing circuit 31, the second voltage dividing circuit 32, and the third voltage dividing circuit 45 may be replaced with two or more resistance elements connected in parallel to each other. Specifically, in a case where the first resistance element R1 and the second resistance element R2 of the first voltage dividing circuit 31 are 990 kΩ and 1 kΩ, respectively, the second resistance element R2 may be replaced with a circuit in which two resistance elements of 2 kΩ are connected in parallel to each other. That is, in the present invention, the configuration of the voltage dividing circuit is not particularly limited.

While the present invention has been described based on the preferred embodiments thereof, the photoacoustic measurement apparatus of the present invention is not limited only to the embodiments described above, and various modifications and changes from the configuration of the above-described embodiments are also included in the scope of the present invention.

EXPLANATION OF REFERENCES

10: photoacoustic image generation apparatus
11: ultrasound probe
12: ultrasound unit
13: laser light source unit
14: display unit
21: reception circuit
22: AD converter
23: reception memory
24: photoacoustic image generation unit
25: ultrasound image generation unit
26: display control unit
27: transmission control circuit
28: control unit
29: display control unit
30: capacitor
31: first voltage dividing circuit
32: second voltage dividing circuit
33: charge control circuit
34: overcharge detection circuit
35: failure detection unit
36: charging circuit
37: power factor improvement circuit
38: thyristor
39: diode
40: inductor
41: discharge control circuit
42: capacitor bank
44: diode
45: third voltage dividing circuit
50: laser chamber
51: laser rod
52: flash lamp
53: first mirror
54: second mirror
55: Q value changing unit
56: Q switch
57: polarizer
58: Q switch driving unit
59: excitation light source power supply unit
101: capacitor
102: voltage dividing circuit
103: charge control unit
104: overcharge detection unit
105: charging circuit
106: power factor improvement circuit
107: thyristor
110: discharge control circuit
111: flash lamp
L: pulsed laser light
L1: wiring
L2: wiring
L3: wiring
M: subject
R01: voltage dividing resistor
R1: first resistance element
R2: second resistance element
R3: third resistance element
R4: fourth resistance element
R5: fifth resistance element
R6: sixth resistance element
Vmax: maximum voltage
Vmon: divided voltage
Vmon1: first divided voltage
Vmon2: second divided voltage
Vmon3: third divided voltage
Vref: reference voltage

What is claimed is:

1. A photoacoustic measurement apparatus, comprising:
a laser light source comprising an excitation light source and a laser medium, the laser light source emitting laser light from the laser medium in response to incidence of excitation light emitted from the excitation light source;
an excitation light source power supply that has a capacitor for supplying a charge voltage to the excitation light source, a charging circuit for charging the capacitor, a plurality of voltage dividing circuits connected to the capacitor in parallel, wherein each of the plurality of the voltage dividing circuits divides the charge voltage, and a failure detection circuit that detects a failure by comparing the divided voltages; and
an ultrasound probe that detects photoacoustic waves generated inside a subject by emission of the laser light emitted from the laser light source to the subject,
wherein the excitation light source power supply further comprises a charge control circuit that controls the charge voltage of the capacitor by controlling the charging circuit and an overcharge detection circuit that detects overcharge of the capacitor,
the plurality of voltage dividing circuits comprises a first voltage dividing circuit and a second voltage dividing circuit,
the charge control circuit controls the charge voltage of the capacitor based on a first divided voltage by the first voltage dividing circuit, and
the overcharge detection circuit detects overcharge of the capacitor based on a second divided voltage by the second voltage dividing circuit.

2. The photoacoustic measurement apparatus according to claim 1,
wherein the failure detection circuit compares the first divided voltage output from the charge control circuit with the second divided voltage output from the overcharge detection circuit.

3. The photoacoustic measurement apparatus according to claim 2,
wherein, in a case where a failure is detected, the failure detection circuit outputs a control signal for stopping the charge voltage from the capacitor to the excitation light source.

4. The photoacoustic measurement apparatus according to claim 2,
wherein each of the voltage dividing circuits is obtained by connecting two resistance elements in series to each other, and a resistance value of a resistance element on a high potential side is larger than a resistance value of a resistance element on a low potential side.

5. The photoacoustic measurement apparatus according to claim 1,
wherein, in a case where overcharge of the capacitor is detected, the overcharge detection circuit outputs a control signal for stopping voltage supply from the capacitor to the excitation light source.

6. The photoacoustic measurement apparatus according to claim 5,
wherein, in a case where a failure is detected, the failure detection circuit outputs a control signal for stopping the charge voltage from the capacitor to the excitation light source.

7. The photoacoustic measurement apparatus according to claim 5,
wherein each of the voltage dividing circuits is obtained by connecting two resistance elements in series to each other, and a resistance value of a resistance element on a high potential side is larger than a resistance value of a resistance element on a low potential side.

8. The photoacoustic measurement apparatus according to claim 1,
wherein, in a case where a failure is detected, the failure detection circuit outputs a control signal for stopping the charge voltage from the capacitor to the excitation light source.

9. The photoacoustic measurement apparatus according to claim 8,
wherein each of the voltage dividing circuits is obtained by connecting two resistance elements in series to each other, and a resistance value of a resistance element on a high potential side is larger than a resistance value of a resistance element on a low potential side.

10. The photoacoustic measurement apparatus according to claim 1,
wherein each of the voltage dividing circuits is obtained by connecting two resistance elements in series to each other, and a resistance value of a resistance element on a high potential side is larger than a resistance value of a resistance element on a low potential side.

11. The photoacoustic measurement apparatus according to claim 1,
wherein the excitation light source power supply is a pulse forming network type flash lamp power supply.

12. The photoacoustic measurement apparatus according to claim 11,
wherein a thyristor is connected to the capacitor, and
a voltage charged in the capacitor is supplied to the excitation light source by applying a gate current to the thyristor.

13. The photoacoustic measurement apparatus according to claim 1,
wherein the capacitor is a capacitor bank, and
the photoacoustic measurement apparatus further comprises a semiconductor switching element that supplies charges accumulated in the capacitor bank to the excitation light source.

14. A photoacoustic measurement apparatus comprising,
a laser light source comprising an excitation light source and a laser medium, the laser light source emitting laser light from the laser medium in response to incidence of excitation light emitted from the excitation light source;
an excitation light source power supply that has a capacitor for supplying a charge voltage to the excitation light source, a charging circuit for charging the capacitor, a plurality of voltage dividing circuits connected to the capacitor in parallel, wherein each of the plurality of the voltage dividing circuits divides the charge voltage, and a failure detection circuit that detects a failure by comparing the divided voltages; and
an ultrasound probe that detects photoacoustic waves generated inside a subject by emission of the laser light emitted from the laser light source to the subject,
wherein the plurality of voltage dividing circuits comprises at least three voltage dividing circuits, and
the failure detection circuit detects a failure by comparing voltages obtained by the at least three voltage dividing circuits and specifies a voltage dividing circuit in which a failure has occurred.

* * * * *